(12) United States Patent
Atkinson

(10) Patent No.: US 7,442,511 B2
(45) Date of Patent: Oct. 28, 2008

(54) ADIPOGENIC ADENOVIRUSES AS A BIOMARKER FOR DISEASE

(75) Inventor: Richard L. Atkinson, Mechanicsville, VA (US)

(73) Assignees: Obetech, LLC, Richmond, VA (US); Obetech Obesity Research, Richmond, VA (US)

( * ) Notice: Subject to any disclaimer, the term of this patent is extended or adjusted under 35 U.S.C. 154(b) by 0 days.

(21) Appl. No.: 11/616,799

(22) Filed: Dec. 27, 2006

(65) Prior Publication Data

US 2007/0218081 A1 Sep. 20, 2007

Related U.S. Application Data

(60) Provisional application No. 60/753,402, filed on Dec. 27, 2005.

(51) Int. Cl.
*C12Q 1/68* (2006.01)
(52) U.S. Cl. ............................................. 435/6; 435/7.1
(58) Field of Classification Search .................. 435/6, 435/7.1
See application file for complete search history.

(56) References Cited

U.S. PATENT DOCUMENTS 6,664,050 B1 * 12/2003 Atkinson et al. ............... 435/6

OTHER PUBLICATIONS

Vangipuram et al. Obesity Research, May 2004, vol. 12, No. 5, pp. 770-777.*

* cited by examiner

*Primary Examiner*—Ali R. Salimi
(74) *Attorney, Agent, or Firm*—Townsend and Townsend and Crew LLP

(57) ABSTRACT

This invention relates to the relationship between infection with adipogenic adenoviruses, such as adenovirus-36 (Ad-36) and the etiologies of obesity and obesity-related cancers and other diseases. Additionally, the invention relates to assaying a subject for Ad-36 status and using Ad-36 status as a marker for the presence of cancer, to predict the future risk of developing cancers, such as breast or prostate cancer, and/or to predict the aggressiveness and prognosis of these cancers.

10 Claims, 17 Drawing Sheets

BODIPY staining of 3T3-L1 cells 5-d post MDI treatment

A. Control, No Ad-36        B. Ad-36 inoculated

ADENOVIRUS - 5 INDUCES OBESITY IN MICE

Results at 27 wk after inoculation:

|  | Control | Ad - 5 infected |
|---|---|---|
| Body wt gain | 18.8 gm | 21.8 gm |
|  | (17.3 - 19.8) | (18.8 - 25.0) |
| % Body fat | 2.4% | 6.7% |
|  | (0.85 - 5.65%) | (3.10 - 11.20%) |

So, et al, Int J Obesity '05

FIGURE 12

VIRAL ANTIBODIES IN HUMANS IN OBESE VS NON-OBESE HUMANS

|  | OBESE AB+/AB- (%) | NON-OBESE AB+/AB- (%) |
|---|---|---|
| Florida | 28/75 (27%) | 5/30 (14%) |
| New York | 43/31 (57%) | 4/39 (9%) |
| Wisconsin | 37/146 (20%) | 7/57 (11%) |
| Totals | 108/254 (30%) | 16/126 (11%) |

FIGURE 13

CHARACTERISTICS OF 26 TWIN PAIRS DISCORDANT FOR AD-36

|  | Antibody + | Antibody − |
|---|---|---|
| Age (yr) | 33.0 ± 15.7 | 33.0 ± 15.7 |
| Sex (% F/M) | 77% / 23% | 77% / 23% |
| BMI: (kg/m$^2$) | 24.5 ± 5.2 | 23.1 ± 4.5* |
| Body fat (%) | 29.6 ± 9.5 | 27.5 ± 9.9* |

ADIPOGENIC ADENOVIRUSES AS A BIOMARKER FOR DISEASE

CROSS-REFERENCE TO RELATED APPLICATIONS

This application is related to and claims benefit under 35 U.S.C. § 119(e) to provisional application Ser. No. 60/753,402, filed Dec. 27, 2005, the disclosure of which is herein incorporated in its entirety herein.

BACKGROUND OF THE INVENTION

1. Field of the Invention

This invention relates to the relationship between infection with adipogenic adenoviruses, such as, for example, adenovirus-36 (Ad-36), and the etiologies of obesity and obesity-related cancers and other diseases. More specifically, the invention relates to methodology for predicting whether a subject is predisposed to developing breast cancer or prostate cancer. Additionally, the invention relates to assaying a subject for Ad-36 status and using Ad-36 status as a marker for the presence of cancer, to predict the future risk of developing such cancer, and/or to predict the aggressiveness and prognosis of cancer.

2. Related Art

There has been a dramatic simultaneous increase in the prevalence of obesity and of certain types of cancer. A worldwide epidemic of obesity accelerated dramatically starting about 1980. In the USA the prevalence of obesity in adults more than doubled in the 20 years from 1980 to 2000 (from 15% to 31%), whereas the prevalence increased only slightly in the prior 20 years from 1960 to 1980 (from 13.5% to 15%). The prevalence of obesity in children tripled from about 1970 to 2000. Likewise, cancers of the breast, prostate, colon, and liver have also rapidly increased in prevalence in recent years.

Changes in reproductive hormones in obesity have been suggested to play a role in the association of breast and prostate cancer (among others) and in the aggressiveness of these cancers. However, changes in reproductive hormones cannot explain cancers such as colon, renal, or pancreatic cancer that are not under hormonal control.

Another possibility for the link between obesity and cancer is the decreased immune function seen in obese individuals. Obese people have a lower antibody response to vaccination with hepatitis B than vaccine people who are not obese. The immune system is critical in inhibiting the growth of neoplasms, so it would not be surprising if this were the mechanism of increased cancers of many types in obesity. However, adenoviruses are well known to decrease immune function as a way to enhance their replication within the host, including human hosts. More relevant, the SMAM-1 avian adenovirus, which has been reported to cause obesity, had a major impact by decreasing immune function of chickens. Thus, there is a direct link between an adenovirus that causes obesity and that also impairs immune function. The inventor has reported that SMAM-1 is associated with obesity in humans, adding a link from adenovirus to human obesity.

Some human adenovirus serotypes are known to be oncogenic, and induce tumors in rats or hamsters. Adenovirus serotypes are divided by Groups. Group A adenoviruses (e.g., Ad-12, Ad-18) are highly oncogenic, producing tumors in most animals within 4 months; group B adenoviruses (e.g., Ad-3, Ad-7) are weakly oncogenic, inducing tumors in most animals within 4 to 18 months; group D viruses are thought to be less oncogenic, but serotype-9 efficiently induces mammary tumors within 3 to 5 months. There has been extensive work on adenovirus-induced cancer, but to date, there has been no evidence that adenoviruses cause human cancer.

If adenoviruses cause human cancers, it is likely that they do so by altering expression of genes in the host that allow unregulated cell growth to occur. Many such tumor markers have been identified. Some are due to genetic variants. Hereditary breast cancer has been linked to germline mutations in one allele of high penetrance susceptibility genes such as BRCA1, BRCA2, CHEK 2, TP53 or PTEN. It is possible that adenovirus infections facilitate cancer in these genetically susceptible individuals. However, adenoviruses may contribute to spontaneous oncogenesis by inducing expression of various oncogenes or suppressing expression of tumor suppressor genes of the host. Among the alterations due to adenoviruses that are thought to contribute to cancer are changes in DNA-dependent protein kinase, fatty acid binding protein, mTOR, p16, p53, PDZ protein, phosphatidylinositol 3-kinase, PML, thymidine kinase, and Zip kinase. Of particular interest are those tumor related factors that are altered by the adenovirus E4 region, and specifically the E4orf1 gene. The E4 oncogenes include DNA-dependent protein kinase, p53, PDZ protein, phosphatidylinositol 3-kinase, PML, thymidine kinase, and Zip kinase. As will be described below, the Ad-36 E4orf1 gene has been shown to be involved in producing obesity by a direct effect on adipocyte metabolism. The E4orf1 region of human adenovirus-5 has been shown to be an oncogene, and a recent paper reported that Ad-5 produces obesity in mice. These findings show a direct link between obesity and cancer, with both being due to a human adenovirus, and provide the likely mechanism via a viral gene.

The general consensus of many investigators in the field of cancer research has been that adenoviruses do not contribute to the etiology of human cancer. Therefore, it would be a major technological advance to demonstrate that adipogenic adenoviruses, such as Ad-36, are associated with obesity-related cancers, such as breast and prostate cancers.

SUMMARY OF THE INVENTION

One aspect of the invention relates to a method for predicting whether a subject is predisposed to developing an adipogenic adenovirus related disease. The methodology includes obtaining a sample from the subject and determining whether the subject is infected with the adipogenic adenovirus by screening for the presence of antibodies specific to the adipogenic adenovirus in the sample and determining the presence of antibodies specific to the adipogenic adenovirus in the sample. The antibodies may be specific to one or more peptide encoded by the nucleic acid sequences SEQ ID NO.:5, SEQ ID NO.:6, and SEQ ID NO.:7. Furthermore, the screening step may be performed by using a method selected from the group consisting of serum neutralization assay and ELISA.

In a further aspect, the adipogenic adenovirus may include adenovirus type 5, adenovirus type 36, and adenovirus type 37. Additionally, the adipogenic adenovirus related disease may include cancer, prostrate cancer, breast cancer, pancreatic dysfunction, pancreatic disease, diabetes, pulmonary disease, brain and nervous system dysfunction, and adrenal dysfunction.

In yet a further aspect, the subject may be a human or an animal. Moreover, the sample may be a biological sample, such as body fluid, a tissue sample, an organ sample, feces, blood, salvia, and any combination thereof.

Another aspect of the invention relates to a method of preventing adipogenic adenovirus related disease in a subject by administering an anti-adipogenic adenovirus vaccine to the subject. The anti-adipogenic adenovirus vaccine may include an effective dose of an active ingredient such as a killed adenovirus type 36, an inactivated adenovirus type 36, a protein or peptide sequence encoding an adenovirus 36 coat protein or fragment thereof, a nucleic acid sequence encoding an adenovirus type 36 coat protein or a fragment thereof, an adenovirus type 36 E1A protein, a genetically modified non-pathogenic virus, and a non-pathogenic virus.

In a further aspect, the vaccine may be administered to the subject intranasally, orally, intravenously, intramuscularly, subcutaneously and/or peritoneally. The subject may be a human or an animal. The adipogenic disease may include cancer, prostrate cancer, breast cancer, pancreatic dysfunction, pancreatic disease, diabetes, pulmonary disease, brain and nervous system dysfunction, and adrenal dysfunction.

Another aspect of the invention relates to a method for determining cancer aggressiveness in a subject. The methodology includes obtaining a sample from the subject and determining whether the subject is infected with the adipogenic adenovirus by screening for the presence of antibodies specific to the adipogenic adenovirus in the sample and determining the presence of antibodies specific to the adipogenic adenovirus in the sample such that the presence of the adipogenic adenovirus correlates with an aggressive cancer. The antibodies may be specific to one or more peptides encoded by the nucleic acid sequences SEQ ID NO.:5, SEQ ID NO.:6, and SEQ ID NO.:7. Furthermore, the screening step may be performed by using a method selected from the group consisting of serum neutralization assay and ELISA.

In a further aspect the adipogenic adenovirus may include adenovirus type 5, adenovirus type 35, and adenovirus type 37. Additionally, the cancer may include breast, prostate, uterus, ovary, colon, kidney, pancreas, and lung.

In yet a further aspect, the subject may be a human or an animal. Moreover, the sample may be a biological sample, such as body fluid, a tissue sample, an organ sample, feces, blood, salvia, and any combination thereof.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

FIG. 12 is a table showing human Ad-5 produced obesity in mice. Also, body fat increased by almost 3 fold.

FIG. 13 is a table showing the presence of serum antibodies to human Ad-36 in people from three US cities. An average of about 30% of obese people were infected with As-36 versus about 11% of non-obese who were not infected with Ad-36.

FIG. 15 is a table showing a comparison of twin pairs discordant for infection with Ad-36. Out of 89 twin pairs, 26 were discordant. The twins infected with Ad-36 were heavier and fatter than their uninfected co-twins.

DETAILED DESCRIPTION OF THE INVENTION

Figure 1:
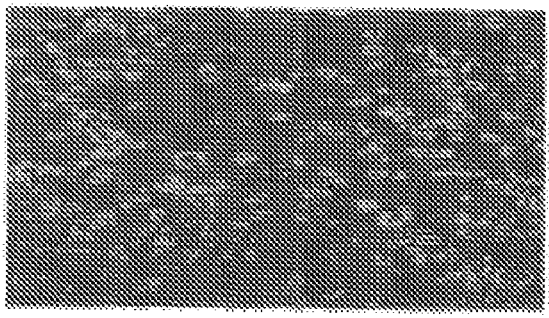
FIG. 1 is a BODIPY staining of 3T3-L1 cells 5 days post MDI treatment. This figure shows triglycerides in 3T3-L1 cells infected with Ad-36 versus uninfected in vitro. Control cells show a moderate BODIPY fat stain whereas Ad-36 infected cells have about twice as much triglyceride, showing adipocyte biochemistry has changed.
Figure 1:
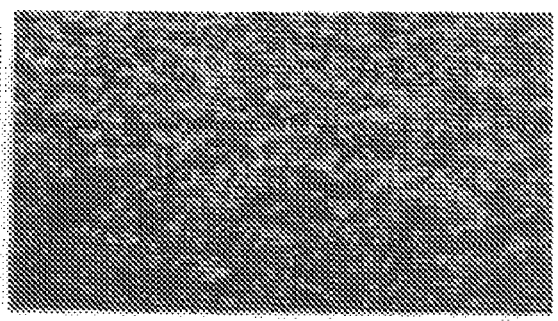

It is understood that the present invention is not limited to the particular methodology, protocols, devices, apparatus, materials, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a virus particle" is a reference to one or more virus particles and equivalents thereof known to those skilled in the art and so forth.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

Any numerical values recited herein include all values from the lower value to the upper value in increments of one unit provided that there is a separation of at least two units between any lower value and any higher value. As an example, if it is stated that the concentration of a component or value of a process variable such as, for example, dosage, dilution, and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically for clarity, but all of the definitions are consistent with how a skilled artisan would understand these terms. Particular methods, devices, and materials are described, although any methods and materials similar or equivalent to those described herein can be used in the practice or testing of the invention.

Definitions

Ad-2 is adenovirus type 2
Ad-5 is adenovirus type 5
Ad-31 is adenovirus type 31
Ad-36 is adenovirus type 36
Ad-37 is adenovirus type 37
BMI is body mass index
FAS is fatty acid synthetase
PPAR is peroxisome proliferator activated receptors
CEBP is CCAAT-enhancer binding protein The term "adipogenic adenovirus" as used herein generally refers to adenoviruses that are capable of stimulating increase lipid production in cells, tissues, and/or organs by turning on the cellular machinery in infected hosts to turn on the host's production of lipogenic enzymes which then produce excess fatty acids and promote fat storage with the infected cells. The adipogenic adenoviruses include without limitation Ad-5, Ad-36, and Ad-37.

The term "BMI" as used herein generally refers to a statistical measure of the weight of a person scaled according to height. BMI may be defined as the individual's body weight divided by the square of the height and may be expressed in the unit $kg/m^2$. BMI may be used as a screening tool to identify possible weight problems for adults and children. However, in order to determine if excess weight is a health risk, a healthcare provider may need to perform further assessments, such as skinfold thickness measurements, evaluations of dies, physical activity, family history, hip to waist ratio, infection with a adipogenic adenovirus, and other appropriate health screenings. For adults 20 years old and older, BMI may be interpreted using standard weight status categories that are the same for all ages and for both men and women. Alternatively, for children and teens, the interpretation of BMI is both age- and sex-specific. For example, an adult having a (i) a BMI less than about 18.5 percent mat be considered underweight, (ii) a BMI is the range of about 18.5 to about 24.9 may be considered normal weight, (iii) a BMI in the range of about 25 to about 29.9 may be considered overweight, and (iv) a BMI greater than about 30.0 may be considered obese.

The term "hip to waist ratio" refers to a measurement that may be used to help determine obesity. The distribution of fat is evaluated by dividing the waist size by the hip size. For example, an individual with about a 30 inch waist and about a 40 inch hip size would have a ratio of about 0.75 and an individual with about a 41 inch waist size and about a 39 inch hip size would have a ratio of about 1.05. The higher the ratio, the higher the risk of heart disease and other obesity-related disorders.

A "biological sample" refers to a sample of tissue or fluid from a human or animal including, but not limited to plasma, serum, spinal fluid, lymph fluid, the external sections of the skin, respiratory, intestinal and genitourinary tracts, tears, saliva, blood cells, tumors, organs, tissue and sample of in vitro cell culture constituents.

An "isolated" or "substantially pure," nucleic acid (e.g., DNA, RNA, or a mixed polymer) for example, is one which is substantially separated from other cellular components which naturally accompany a native human or animal sequence or protein, e.g., ribosomes, polymerases, many other human or animal genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

The term "immunogenic," generally refers to an anti-obesity vaccine that has the capability to provoke in an immunized animal, an immune response that yields neutralizing antibodies against an obesity-causing, live virus that might infect the person after administration of the vaccine.

The term "antibody" refers to antibodies, digestion fragments, specified portions and variants thereof, including antibody mimetics or comprising portions of antibodies that mimic the structure and/or function of an antibody or specified fragment or portion thereof, including single chain antibodies and fragments thereof. The invention encompasses antibodies and antibody fragments capable of binding to a biological molecule (such as an antigen or receptor), such as the fiber coat protein of adenoviruses, and specifically, Ad-36, or portions thereof.

The term "nucleic acid sequence," includes an oligonucleotide, nucleotide, or polynucleotide, and fragments thereof, and to DNA or RNA of genomic or synthetic origin which may be single- or double-stranded, and represent the sense or antisense strand, to peptide nucleic acid (PNA), or to any DNA-like or RNA-like material, natural or synthetic in origin.

Fragments: include any portion of a heterologous peptide or nucleic acid sequence. Heterologous peptide fragments retain at least one structural or functional characteristic of the subject heterologous polypeptides. Nucleic acid sequence fragments are greater than about 60 nucleotides in length, and most preferably includes fragments that are at least about 100 nucleotides, at least about 1000 nucleotides, and at least about 10,000 nucleotides in length.

Complementary or complementarity: as used herein, include the natural binding of polynucleotides under permissive salt and temperature conditions by base-pairing. For example, the sequence "A-G-T" binds to the complementary sequence "T-C-A."

Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of molecules.

Functional equivalent: a protein or nucleic acid molecule that possesses functional or structural characteristics that are substantially similar to a heterologous protein, polypeptide, enzyme, or nucleic acid. A functional equivalent of a protein may contain modifications depending on the necessity of such modifications for the performance of a specific function. The term "functional equivalent" is intended to include the "fragments," "mutants," "hybrids," "variants," "analogs," or "chemical derivatives" of a molecule.

Protein purification: broadly defined, any process by which proteins are separated from other elements or compounds on the basis of charge, molecular size, or binding affinity.

Substantially purified: as used herein, includes nucleic or amino acid sequences that are removed from their natural environment, isolated or separated, and are at least 60% free, preferably at least 75% free, and most preferably at least 90% free from other components with which they are naturally associated.

Inhibition: as used herein, refers to a reduction in the parameter being measured, whether it be adenovirus type 36 growth or viability. The amount of such reduction is measured relative to a standard (control). "Reduction" is defined herein as a decrease of at least around 25% relative to control, preferably at least around 50%, and most preferably of at least around 75%.

The anti-adipogenic adenovirus vaccines of the invention, wherein the immunogenic component is live, inactivated virus, killed virus, coat protein per se, epitope-comprising coat protein segment, or coat protein (or epitope-comprising segment thereof) provided with use of a non-pathogenic, genetically modified carrier virus such as a vaccinia virus or a fowl pox virus, are prepared using methods well known in the art. Thus, the vaccines will include carriers, excipients, adjuvants, antimicrobials, preservatives and the like as well understood in the art. Thus, in addition to the active ingredient, the vaccines will have suitable compositions, usually aqueous buffers, such as phosphate-buffered saline or the like, in which the active ingredient will be suspended along with, optionally, any of various immune-system stimulating adjuvants used in human vaccine preparations, antimicrobial compositions, and other compositions to stabilize the preparations. All compositions included with the vaccine preparation will be suitable for administration to humans. The vaccine preparation may be stored in lyophilized form and then combined with solution soon before administration. For oral administration, the vaccine preparation may be in solution, tablet or pill form optionally with an enteric coating as understood in the art. The concentration of active (immunogenic or immunogen-providing) component in solution with which it is administered typically will be between about 1 ng and about 1 mg/ml.

The anti-adipogenic adenovirus vaccines of the invention will be administered intranasally, orally, or by injection intravenously, intramuscularly, subcutaneously or peritoneally. Administration of the vaccines of the invention is to be under the guidance of a physician.

Appropriate dosing of the anti-adipogenic adenovirus vaccine is well within the skill of medical practitioners and will depend on a number of factors including the age of the person being treated, the urgency of the person's developing protective immunity, the status of the person's immune system, and other factors known to the skilled. The vaccine typically will be administered in several steps in order to cause and maintain protective immunity against obesity-causing virus in the person being vaccinated. Thus, after the primary vaccination, there typically will be between one and about ten booster vaccinations separated by periods between about 1 week and 10 years.

A single dose of an anti-obesity vaccine of the invention (in solution form) will have a volume of between about 0.1 ml and 10 ml and, in any form, will have between about 1 ng and 10 mg of killed or inactivated adipogenic virus, between about 1 ng and 10 mg of genetically modified, non-pathogenic virus, or between about 1 ng and 10 mg of coat protein (e.g., fiber protein) or 6-30 amino acid peptide (in its form as modified to be immunogenic).

An anti-adipogenic adenovirus vaccine of the invention, wherein the active ingredient is nucleic acid, will also be a standard preparation for vaccines of that type. With vaccines of this type, the nucleic acid is not the immunogen but is expressed in vivo after administration of the vaccine as a peptide or protein which in turn is immunogenic. Vaccines of this type will be administered by techniques known in the art for such vaccines (e.g., intramuscular injection). Dosing will also be according to procedures known in the art to cause and maintain protective immunity against viral obesity in the vaccinated individual.

Note that an anti-adipogenic adenovirus vaccine according to the invention may include active ingredients based on more than one adipogenic virus (or the coat protein (e.g. fiber protein) or epitopic segments of the coat protein thereof).

In yet another aspect, the invention is a method of preventing adipogenic adenovirus related disease caused by a virus in a human susceptible thereto which comprises administering to the human an amount of an anti-adipogenic adenovirus vaccine of the invention that is effective to raise and maintain a protective immune response against an adipogenic adenovirus.

This invention generally relates to the relationship between infection with human adipogenic adenoviruses, such as Ad-5, Ad-36, and Ad-37, the etiologies of obesity, and the dysfunction of cells, tissues and/or organs, such as cancers, dysfunction of the pancreas, dysfunction of skeletal and cardiovascular muscle, pulmonary dysfunction, dysfunction of the brain and nervous system, and adrenal disease and dysfunction. Moreover, the invention relates to utilizing adipogenic adenovirus status as a predictor for disease status, prognosis, treatment outcome, and prevention of infection and disease.

The main mechanism of adipogenic adenovirus-related disease is the production of lipids within cells. The adipogenic adenoviruses are capable of changing the cellular machinery in infected subjects to turn on the host's production of lipogenic enzymes. As a result, the lipogenic enzymes make excess fatty acids and promote fat storage within the cells of multiple organs.

Multiple cells of the body are known to have the capacity to make fatty acids within their cells. Fatty acid synthetase (FAS) is one of the most important lipogenic enzymes and is expressed in a number of adult and fetal cells, which suggests that these tissues are capable of producing fatty acids. For example, FAS is expressed in adult cells such as epithelial cells of the duodenum and stomach, hemopoietic cells, appendix, ganglion cells of alimentary tract, hepatocytes, mast cells, seminal vesicle, umbrella cells of urinary bladder, adrenal zona fasciculate cells, adipocytes, anterior pituitary cells, basket cells of cerebellum, cerebral cortical neurons, deciduas, decidualized stromal cells of endometrium, epithelial cells of apocrine gland, duct and acinus of breast, prostate, and sebaceous gland, letein cells, and Type II alveolar cells of lung.

Additionally, FAS is also expressed in fetal cells such as anterior pituitary cells, chondrocytes of tracheobronchial wall, endothelium of blood vessels and heart, epithelial cells of bronchus, esphagogastrointestinal tract, lung, pancreas, prostate, thyroid, tongue, trachea, proximal tubules of kidney, fibroblasts, nodal lymphocytes, neuroblasts in adrenal medulla, thymocytes, striated myocytes of tongue, epithelial cells of salivary glans and tracheobronchial glands, hemopoietic cells, heptocytes, Lanhans cells of chorionic villi, osteoblasts, perivertebral fibroblastic cells, Schwann cells of sympathetic ganglion and Auerbach plexus, subcapsular cells of adrenal, adipocytes, Leidig cells of testis, mast cells, uroepithelium of urinary tract, and adrenocortical cells of upper layer.

While fatty acids are critical to the intracellular milieu for many biochemical processes, excess fatty acids within the cells profoundly alter cellular biochemistry. Excess fatty acids within cells may lead to abnormal functioning of a number of intracellular processes. For example, excess fatty acids in pancreatic tissue reduce insulin secretion, and fatty acids in cancer cells provide the major source of energy for cancer growth. Moreover, fatty acids within the lung cells stimulate attraction of macrophages to the area and are associated with asthma and emphysema. Therefore, adverse results occur when cells are exposed to excess to fatty acids.

According to one embodiment, adipogenic adenoviruses may be a mechanism by which excess fatty acids and triglycerides are produced in cells and tissues. Studies have demonstrated that adipogenic adenoviruses can alter lipogenic enzymes in adipose tissue and in liver. For example, other studies have shown that infection with the adipogenic adenovirus, Ad-36, stimulates the rapid appearance of differentiation factors including glycerol-3-phosphodehydrogenase, PPAR-gamma, CEBP-alpha and beta, and lipoprotein lipase in 3T3-L1 cells. Since multiple tissues accumulate adipogenic adenoviral DNA, excess lipogenic enzymes may be present in all infected tissues that are capable of producing these enzymes.

According to another embodiment of the invention, adipogenic adenovirus infection may be used to determine the presence of an obesity-related cancer. In a further embodiment, adipogenic adenovirus infection may be used to determine whether a subject is predisposed to developing an obesity-related cancer.

The prevalence of multiple types of cancers is increased in obese people. These cancers include without limitation breast, prostate, uterus, ovary, colon, kidney, pancreas and lung. Hepatocellular cancer may also be linked to obesity and the metabolic syndrome. Additionally, obesity may be linked to the aggressiveness of some types of cancer and to a poorer prognosis. For example, obesity may be associated with a higher grade of prostate cancer and higher recurrence rates after radical prostatectomy. Also, in non-Hispanic White women, breast tumor size correlates with obesity. Specifically, this is most notable for the highest quartile of waist circumference where the odds ration is 2.76.

Studies have shown that fatty acids are the substrate for energy expenditure in cancer cells and that blocking FAS can block cancer growth. Moreover, it has been shown that FAS is increased in many obesity-related cancers and that FAS favors tumor growth. Adipogenic adenovirus infection in cancer cells may stimulate fatty acids in cell thereby promoting cancer growth by providing an energy source for the cancer cells.

FAS expression has been detected in various tumors and associated with histological subtype, histopathological grade and tumor aggressiveness. Studies have demonstrated that FAS is highly expressed in human neoplasm such as breast, prostate, ovarian, colorectal, and endometrial cancers. It has been determined that FAS (OA-519) was a predictor of prostate cancer. It was observed that OA-519 immunoreactivity was seen in 56 (57%) of the 99 primary prostate cancers examined. OA-519 cancers were more likely to progress than the non-OA-519 cancers.

Indeed, the presence of Ad-36 was confirmed in 61% of human prostate cancer tissues and it was observed that 50% and 51% of breast and prostate cancer patients, respectively, have antibodies to Ad-36 in comparison to 13.8% of the normal population.

Therefore, the presence of FAS in prostate cancer tissue in approximately the same number of cancer patients as were observed to be infected with Ad-36 in combination with the findings that adipogenic adenoviruses increase FAS in cells and that inhibition of FAS may inhibit cancer, suggest that infection of an adipogenic adenovirus cause both obesity and obesity-related cancer in a subject.

According to an embodiment of the invention, the prevalence of Ad-36 infection may be statistically higher in patients with breast and prostate cancer than in individuals without cancer. In a further embodiment, Ad-36 status may serve as a marker for breast and prostate cancer. Yet a further embodiment relates to patients with breast or prostate cancer who have Ad-36 DNA in their tissues will have more aggressive cancer and/or a poorer prognosis than those without Ad-36 DNA.

According to another embodiment of the invention, adipogenic adenovirus infection may be used as a predictor for disease prognosis, treatment prognosis, or as a predictor of tumor aggressiveness. In breast, prostate and ovarian carcinomas, high levels of FAS are often associated with poor prognosis. The association between FAS expression and tumor size or a marker of proliferative activity of tumor cells may suggest that FAS is related to growth and proliferation of these malignant tumors.

For example, studies have shown that overexpression of FAS increased heptacarcinogenesis in rat. Other studies have shown that about 30% of patients with early breast cancers expressed FAS. The patients with breast cancer expressing FAS had significantly higher tumor grade, larger tumor volume, advancing clinical stage, and Gleason's score, one of the most powerful predictors. FAS expression has also been studied in ovarian neoplasia, where it was seen to be associated with histological tumor grade and shorter survival. Moreover, studies have shown that overweight and obese individuals had significantly increased mortality from multiple types of cancer in humans.

FAS is associated with colon cancer and with its severity. Studies have shown that only 2 (5%) of 43 adenomas with low-grade dysplasia showed reactivity for FAS. However, positive FAS immunostaining was seen in 7 (17%) of 40 cases of adenomas with moderate-grade dysplasia, in 9 (53%) of 17 cases of adenomas with high-grade dysplasia, and in 81% of adenocarcinomas (p<0.0001).

Therefore, one embodiment of the invention is directed to a diagnostic screening test for the presence of adipogenic adenovirus infection in a subject. If the subject tests positive for adipogenic adenovirus, FAS expression may be increased in cancer cells resulting in a more aggressive cancer and/or a poorer prognosis. Other information linking Ad-36 and cancer is the finding of unique sequences of Ad-36 DNA in obesity-related cancers, such as prostate cancer tissue by polymerase chain reaction test (PCR). The unique sequences of DNA from Ad-36 fiber protein, which are described in Assignee's previous U.S. Pat. Nos. 6,664,050 and 6,127,113 were detected in 11 of 18 samples of prostate cancer tissue. Exemplary screening techniques are described below.

The adipogenic adenovirus test will be useful in two ways. If a subject with a breast lump or an enlarged prostate has a positive adipogenic adenovirus test (tested by, for example, either a positive serum test or a positive PCR tissue test), there is a higher risk that the subject has cancer and tests should be done to evaluate for cancer (e.g., biopsy) rather than "watchful waiting." Conversely, if a person has a positive adipogenic adenovirus test, then the subject should be screened for cancer at more regular intervals than a person with a negative Ad-36 test.

A vaccine against Ad-36 has been developed in rabbits using killed virus. Serum from the rabbits contains antibodies that prevent Ad-36 growth in tissue culture in up to 17 serial dilutions (a dilution of 1:131,072 of the original concentration). It is known that the only effective antibodies against adenovirus growth are directed against segments of fiber protein of the various adenoviruses (neutralizing antibodies). Ad-36 antibodies do not cross react with any other adenoviruses, so unique DNA sequences in Ad-36 fiber protein are responsible for this specificity. Three sequences in Ad-36 fiber protein that are unique to Ad-36 have been identified. Using standard technology in the field, peptides from these sequences will be used to make a highly purified vaccine that should have minimal allergic reactions. The peptides will be bound to adjuvants commonly used in vaccines to enhance effectiveness. These techniques are known by those of skill in the art.

In a particular embodiment, a vaccine against adipogenic adenoviruses, such as Ad-36 to prevent cancer may be made. Since adipogenic adenoviruses are associated with cancer, a vaccine against adipogenic adenoviruses may be used to prevent cancer. For example, a vaccine against Ad-36 using unique DNA sequences contained in the fiber protein DNA to make peptides may be developed. This technology is known by those of skill in the art.

In a further embodiment, a novel concept of sequencing the fiber protein DNA from all of the adipogenic adenoviruses to determine their structures may be performed. Following sequencing, the DNA sequences that are present in many or all of the fiber proteins will be identified using DNA comparison databases commonly used in the field. This may be accomplished by, for example, employing GenBank to identify the unique sequences in Ad-36 fiber protein DNA. DNA sequences of about 30-75 base pairs that code for peptides of about 10-25 amino acids are then selected. It is known that peptides in the knob portion of the fiber protein are effective, so these sequences will be examined. Following identification, the peptides may be coupled with adjuvants to make a vaccine that will prevent infection from any of the human adenoviruses. The usefulness of a common vaccine for the adipogenic adenoviruses will be to prevent obesity, cancer, and other human diseases that are due to adipogenic adenoviruses. For example, a significant percentage of military recruits contract adenovirus infections during basic training. Also, many of the mild illnesses associated with fever, cough, diarrhea, or conjunctivitis in the first two years of life are due to adenoviruses.

According to one embodiment of the invention, adipogenic adenovirus infection may be used as a predictor of the development of obesity and diseases due to the complications of obesity and the outcome of regimens that affect body weight. Complications of obesity may include, inter alia, diabetes mellitus, hypertension, hyperlipoproteinemia, cardiac disease such as atherosclerotic disease and congestive heart failure, pulmonary diseases such as sleep apnea and asthma, cerebrovascular accidents, cancers such as breast, uterus colon and prostate cancer, gall bladder disease such as stones and infection, toxemia during pregnancy, risks during surgery, gout, decreased fertility, degenerative arthritis, and early mortality.

It has been demonstrated by the Assignee that human Ad-36 stimulates the storage of fat and formation of new fat cells in mouse preadipocytes (3T3-L1 cells) (FIG. 1) and in human preadipocytes. Additionally, Assignee has demonstrated in U.S. Pat. Nos. 6,127,113 and 6,664,050, herein incorporated in their entirety by reference, that Ad-36 infection is associated with obesity. For example, four experiments were conducted in chickens, one experiment in mice, and two experiments in monkeys, all showing that infection with Ad-36 increased body fat and lowered serum cholesterol and triglycerides. Most notable, food intake measured in chickens, mice, and rats was not difference between infected and control animals indicating that energy expenditure was different. The mechanism of Ad-36 has a direct effect on adipocytes to increase lipogenic enzymes and differentiation factors. Cells infected with Ad-36 exhibited about 2 times as much stored triglyceride at 5 days.

Figure 2:
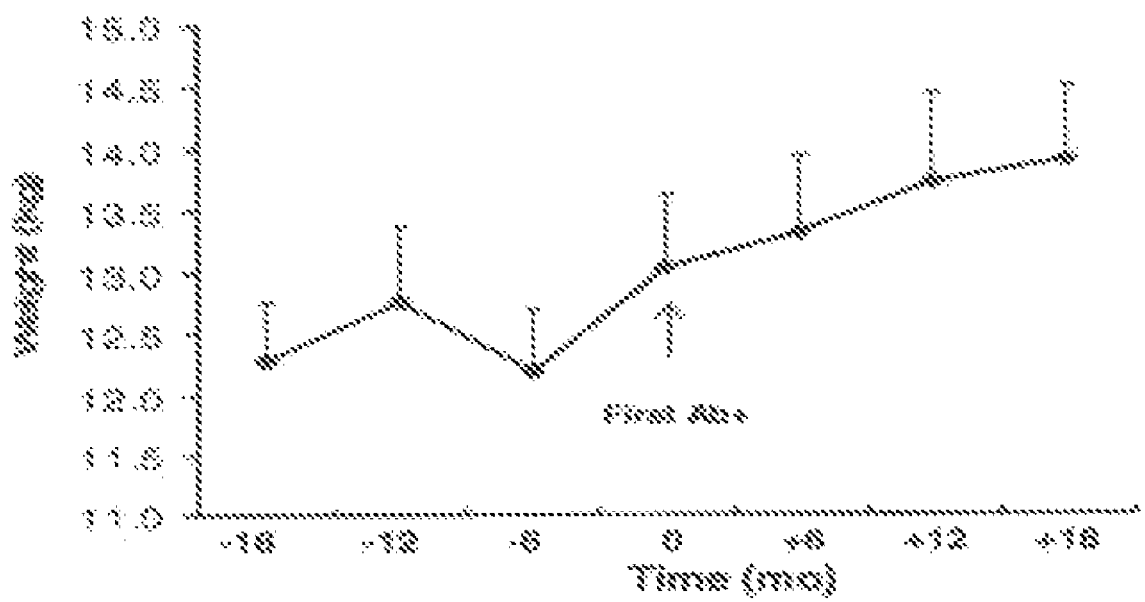
FIG. 2 is a graph showing the effects of spontaneous infection with Ad-36 in ad libitum fed rhesus monkeys. As compared to the period before a monkey became infected, once infection was noted (designated ↑) there was a steady rise in body weight that was still rising at about 18 months.
Figure 3:
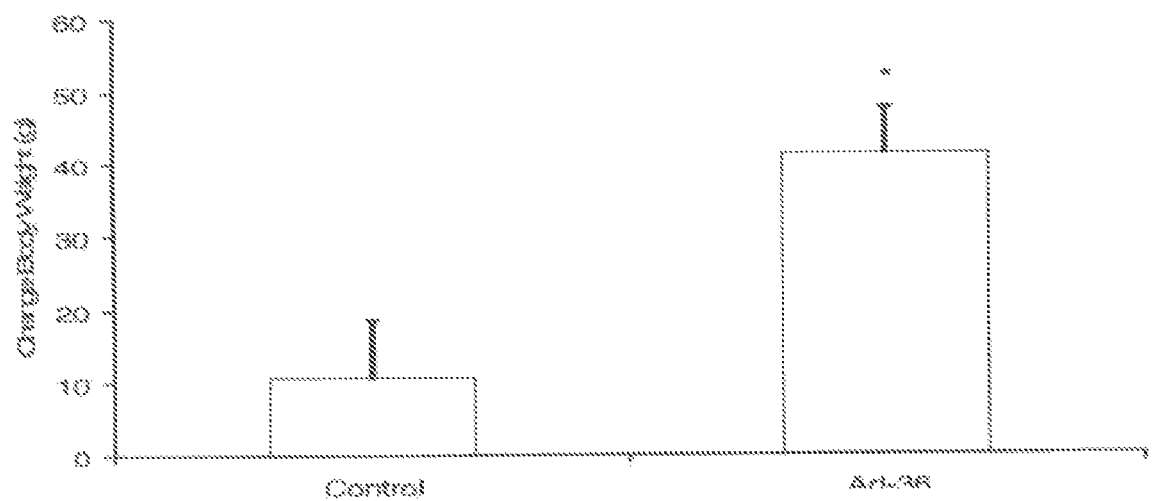
FIG. 3 is a graph showing an increase in body weight in monkeys infected with Ad-36. As compared to uninfected monkeys, infected monkeys gained about four times as much weight in about seven months.
Figure 4:
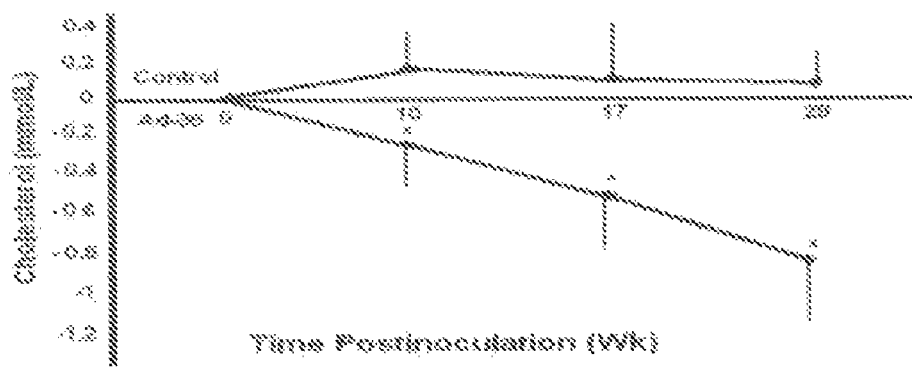
FIG. 4 is a graph showing a decrease in serum cholesterol in Ad-36 infected marmoset monkeys. Serum cholesterol began dropping immediately after infection and by about 10 weeks. This is significantly different than baseline in infected monkeys. There is no change in uninfected monkeys.
Figure 5:
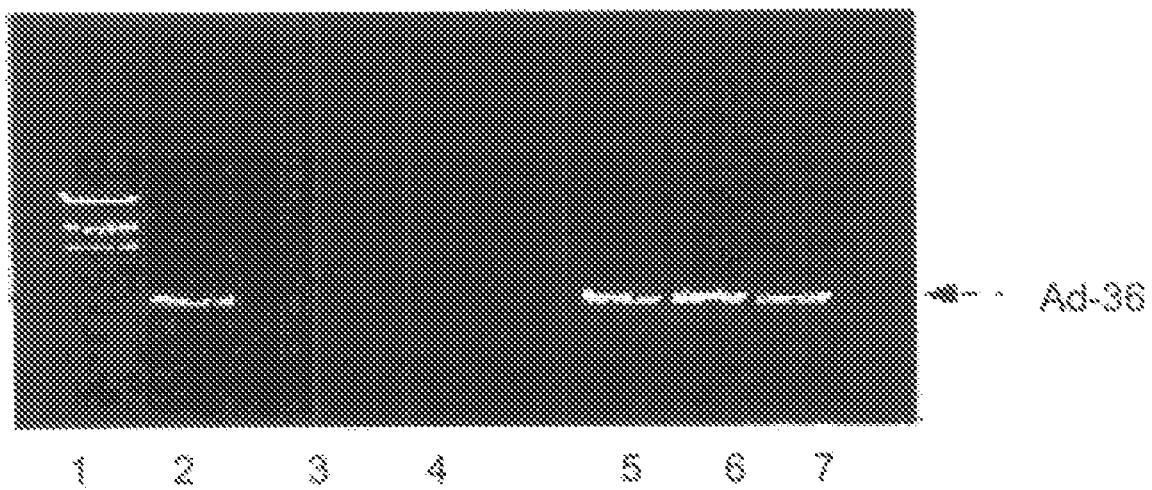
FIG. 5 is a gel showing the presence of Ad-36 DNA in adipose tissue of infected marmosets using a nested PCR assay. Lane 1 is Ad-36 DNA, lanes 2-4 show no Ad-36 DNA in fat of uninfected monkeys, and lanes 5-7 shows the presence of Ad-36 DNA in all infected monkeys.
Figure 6:
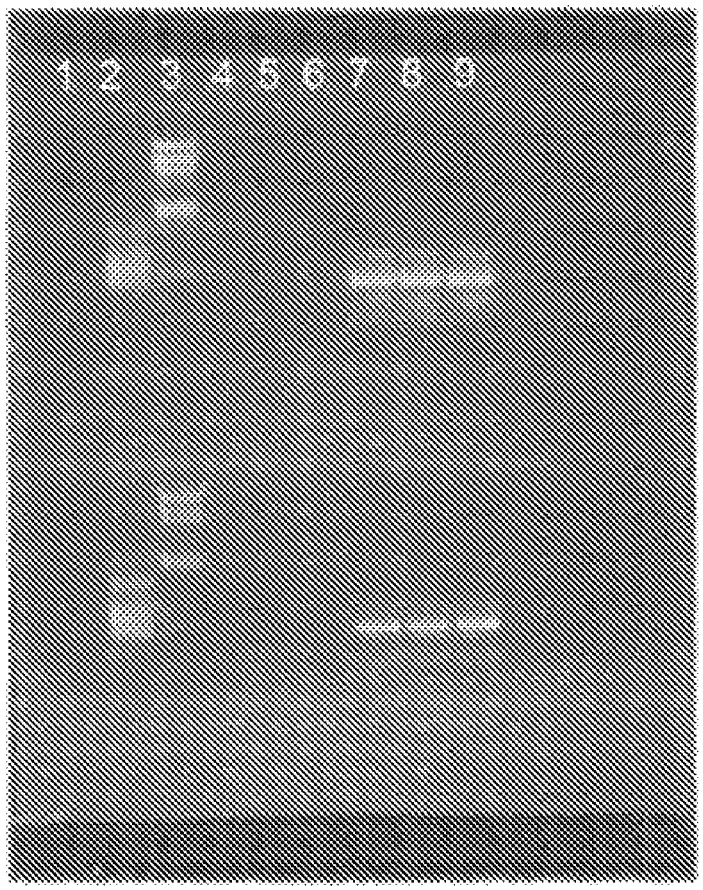
FIG. 6 is gel showing Ad-36 DNA in liver (upper lanes) and muscle tissue (lower lanes) of infected marmosets using nested PCR assay. Ad-36 DNA from infected monkeys is seen in lanes 7-9 of liver tissue and muscle tissue and is not present in lanes 4-6 from uninfected monkeys. Lane 2 is Ad-36 from culture, lane 3 is marker.
Figure 7:
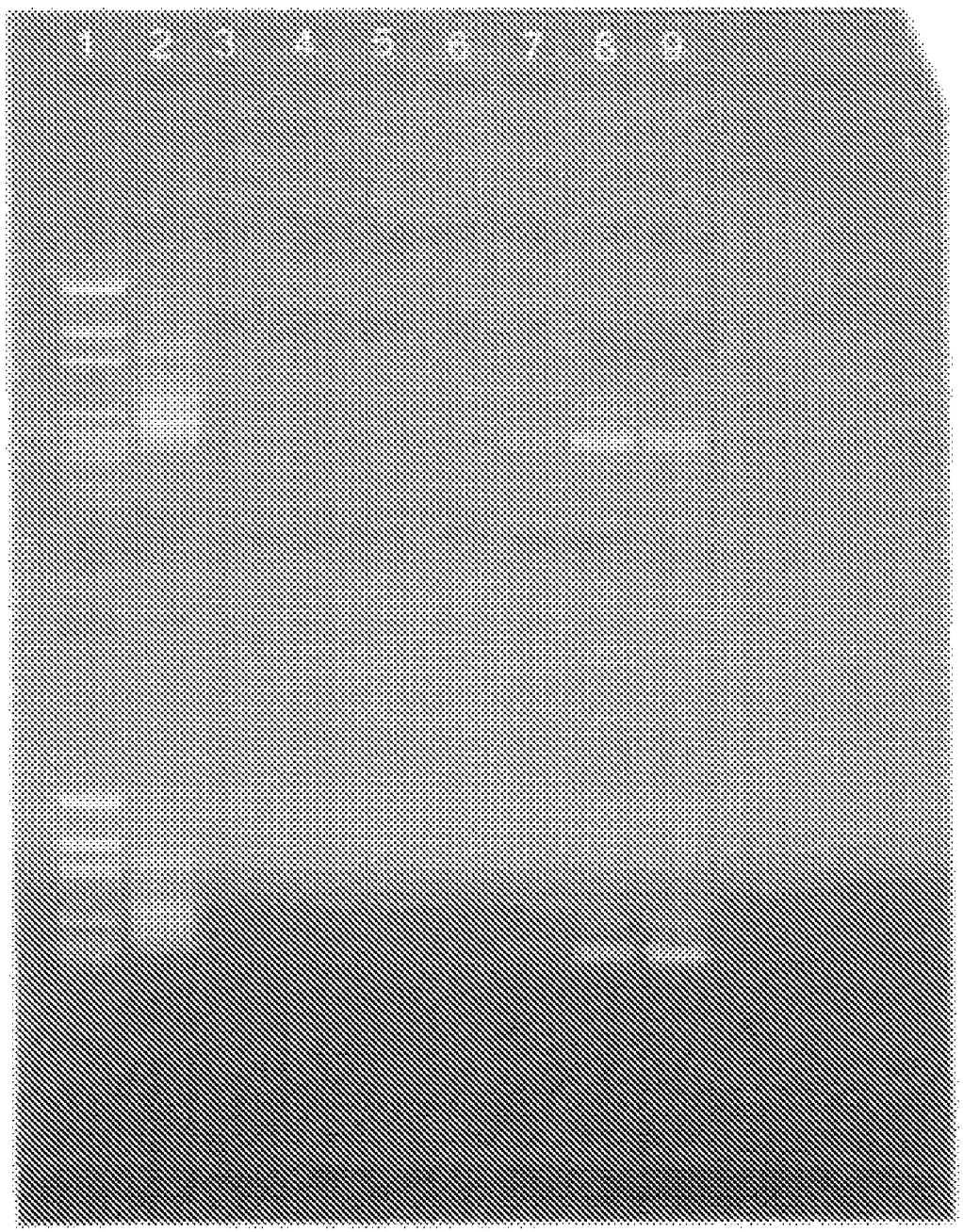
FIG. 7 is a gel showing Ad-36 DNA in brain and muscle tissue of infected animals by nested PCR assay. Upper lanes are brain tissue from marmosets, lower lanes are muscle tissue. Ad-36 DNA from infected marmosets is seen clearly in lanes 8-9 and more faintly in lane 7. Ad-36 DNA is not present in lanes 4-6 from non-infected marmosets. Lane 2 is positive control from Ad-36 culture.
Figure 8:
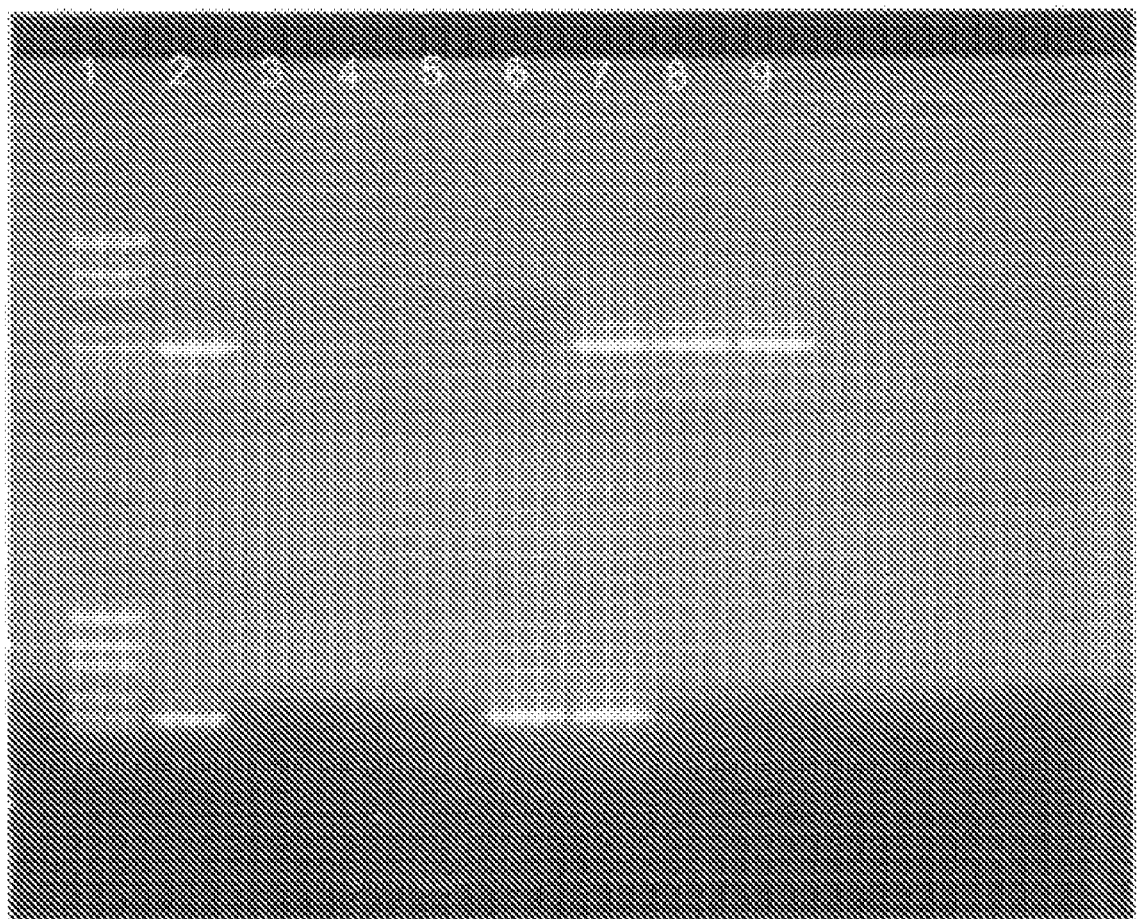
FIG. 8 is a gel showing Ad-36 DNA in adipose tissue of humans using nested PCR assay (bottom lanes). This gel shows Ad-36 DNA in adipose tissue of marmosets in the upper lanes (repeat of data in FIG. 5: lanes 4-6 negative from control marmosets, lanes 7-9 Ad-36 DNA from infected marmosets). In bottom lanes Ad-36 DNA is seen in 2 of 6 samples of human visceral adipose tissue obtained from cadavers at autopsy (lane 2 is positive control, lanes 6-7 are Ad-36 positive, lanes 4, 5, 8, 9 are negative).

A large number of studies were also performed with the adipogenic adenovirus, Ad-36. Rhesus monkeys that were spontaneously infected with Ad-36 showed a significant weight gain in 18 months after infection (FIG. 2). Marmosets were also infected with Ad-36 and a four-fold weight gain was observed in infected marmosets in comparison to uninfected marmosets (FIG. 3). Moreover, body fat increased by about 70% and serum cholesterol dropped by about 35 mg/dl after infection (FIG. 4). Notably, Ad-36 DNA was observed in multiple tissues of the monkey, such as brain, liver, lung, muscle and adipocyte tissue seven months following initial infection and was no longer able to grow the virus from the blood or feces of the infected monkeys after two months (FIGS. 5-7). Ad-36 DNA has also been observed in human adipocyte tissue as seen in FIG. 8.

Figure 9:
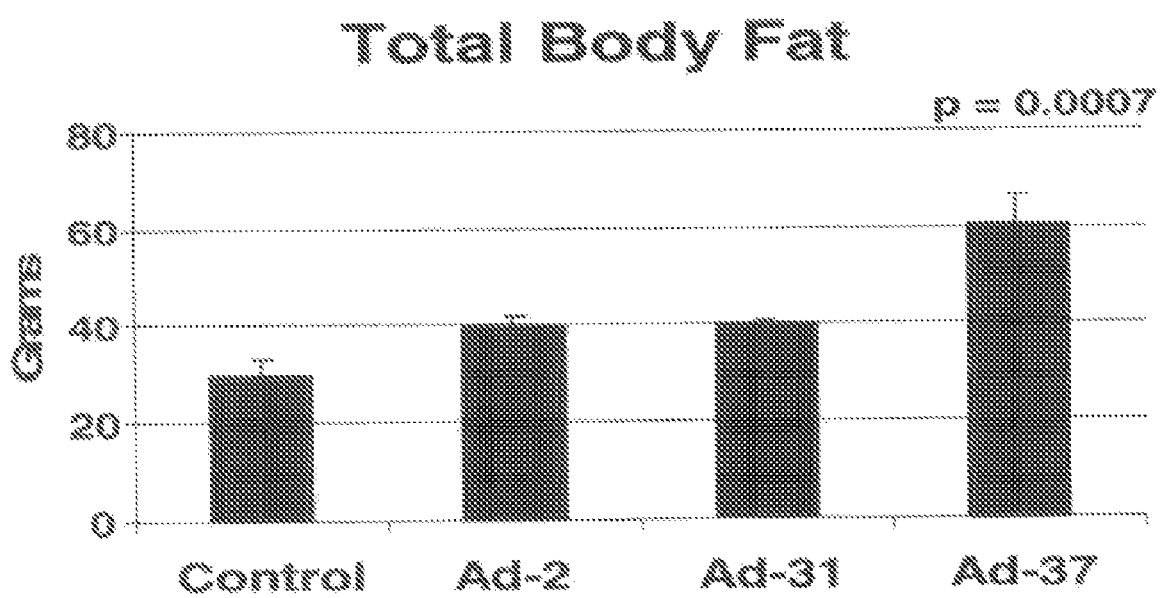
FIG. 9 is a chart showing the effects of multiple human adenoviruses on total body fat in chickens. Ad-2 and Ad-31 did not increase body fat, but Ad-37 had a marked effect.
Figure 10:
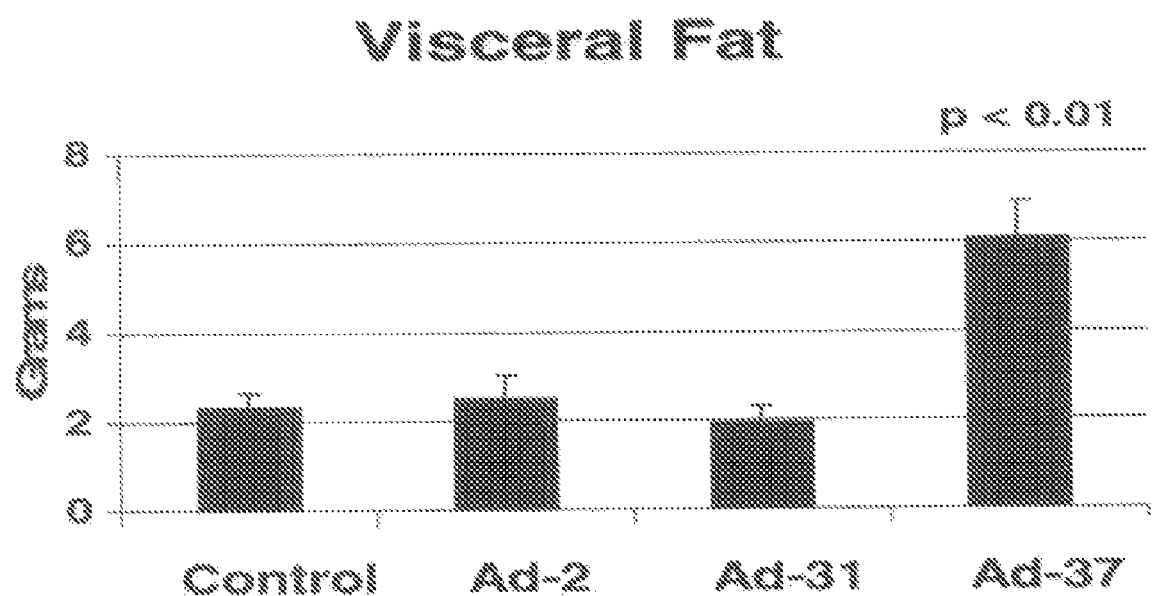
FIG. 10 is a chart showing the effects of multiple human adenoviruses on visceral fat in chickens. Ad-2 and Ad-31 did not increase visceral fat, but Ad-37 had a marked effect.
Figure 11:
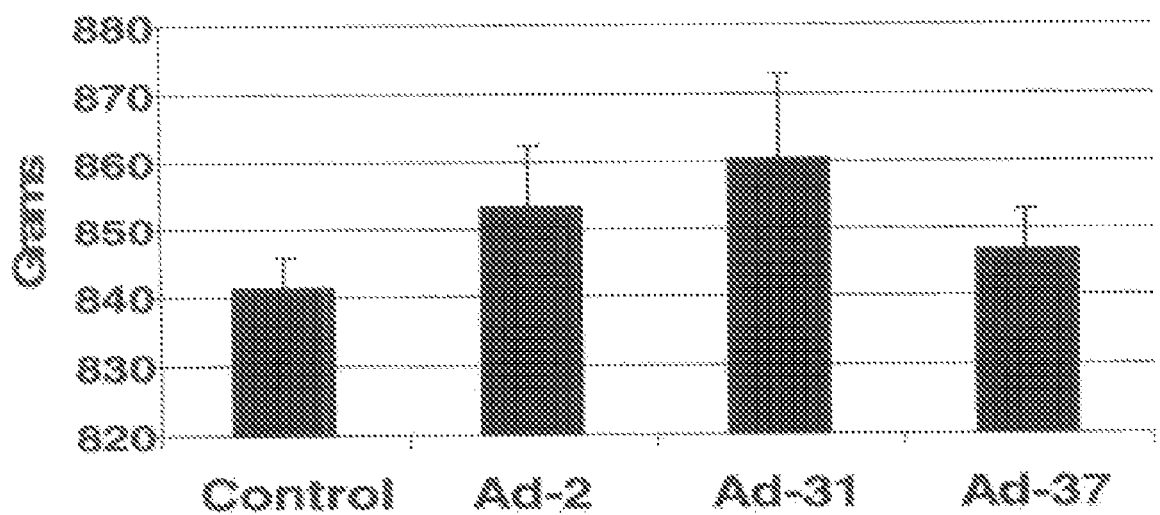
FIG. 11 is a chart showing food intake in animals exposed to multiple human adenoviruses. There were no differences in cumulative food intake among groups, yet individuals infected with Ad-37 became obese while individuals infected with Ad-2 or Ad-31 were not.

Other studies have demonstrated that Ad-37 caused obesity in chickens, but Ad-2 and Ad-31 did not (FIGS. 9-11). Cumulative food intake was not different among the groups studied. Moreover, studies have also demonstrated that Ad-5 caused obesity in mice (FIG. 12). These studies show that stimulation of lipogenic enzymes and obesity are not non-specific effects of all adenovirus infections, but multiple adenoviruses may do so.

Another embodiment of the invention includes using adipogenic adenoviruses to predict diabetes and other pancreatic dysfunction. Additionally, another embodiment is directed to a vaccine against adenoviruses that may prevent pancreatic disease, including some cases of diabetes.

Pancreatic beta cells make lipids and lipid metabolism in the beta-cell is critical for the regulation of insulin secretion. Enzymes that are associated with lipid synthesis or oxidation cause a decrease in the amount of insulin produced and secreted. Studies have demonstrated that overexpression of SREBP-1 in beta cells decreases insulin synthesis. SREBP-1 is a direct precursor of FAS and has been found to be increased by adenovirus infection in vitro and in vivo in hepatocytes. Other studies have demonstrated that carbohydrate responsive element-binding protein (ChREBP) binding to fatty acid synthase and L-type pyruvate kinase genes is stimulated by glucose in pancreatic beta-cells. Higher carnitine palmitoyltransferase I (CPT I) protein levels in beta cells causes a decrease in secretion of insulin in response to glucose. Adipogenic adenoviruses may cause diabetes because they increase obesity and produce insulin resistance, but the changes in lipogenic enzymes due to virus infection of the pancreas also may play a role.

An additional embodiment of the invention is for using adipogenic adenoviruses status to predict liver disease, cirrhosis, and other liver dysfunction. Also, a vaccine against adenoviruses may be used to prevent liver diseases due to adipogenic adenoviruses.

Obesity is associated with liver disease. The spectrum of liver disease with obesity starts with fat infiltration of the liver, progresses to steatohepatitis (non-alcoholic steatohepatitis=NASH), and a sizeable percentage of patients with NASH go on to develop cryptogenic cirrhosis. The frequency and severity of fatty infiltration of the liver goes up with increasing body weight and is present in the vast majority of patients with morbid obesity. It has been reported that obesity is present in about 30% to about 100% of the cases of non-alcoholic fatty liver disease (NAFLD). Other studies have demonstrated that greater than about 95% of subjects with severe obesity had various degrees of fatty infiltration of the liver and about 65% had NASH.

Adipogenic adenoviruses produce increased levels of lipogenic enzymes and an accumulation of fat in the liver. As noted above, fatty infiltration of the liver may lead to cirrhosis. There are a number of causes of fatty infiltration of the liver, and additional insults to the liver may increase the chance that cirrhosis will occur. Individuals with risk factors for liver disease or with abnormal liver function tests should be tested for adipogenic adenoviruses as they may need special attention to prevent progression of fatty liver to cirrhosis. A vaccine against adipogenic adenoviruses may reduce or prevent many cases of fatty liver and cirrhosis.

Yet another embodiment of the invention includes using adipogenic adenoviruses to predict muscle dysfunction. Also, a vaccine against adenoviruses may be used to prevent muscle dysfunction.

Muscles are known to have lipogenic enzymes present and to store intracellular lipids. Obesity is associated with abnormal lipid metabolism and accumulation of intramuscular lipid. Studies have shown that a lipogenic gene, stearoyl-CoA desaturase 1 (SCD1), is up-regulated in skeletal muscle from extremely obese humans. High intramuscular fat is related to poor muscle function in obese people and is related to insulin resistance and diabetes. Other studies have showed that insulin resistance and type 2 diabetes result from the accumulation of lipids in tissues not suited for fat storage, such as skeletal muscle and the liver. FFAs stimulated the de novo synthesis of ceramide and sphingosine, two sphingolipids shown previously to inhibit insulin action. The inability to transition from fat to glucose as the primary source of fuel may be associated with insulin resistance, metabolic dysregulation, and cardiovascular risk. Since leptin has been shown to go down in adipocytes infected with Ad-36, this might produce insulin resistance.

Obese people complain of pain with exercise. The reasons for this are not clear, but obese individuals have more intramuscular lipids and a lower exercise capacity. The intramuscular lipids alter the substrate utilization of skeletal muscles. Increased intramuscular lipids due to adipogenic adenoviruses may limit exercise capacity, increase pain, and alter substrate utilization. This would be particularly important in animals used for performance or endurance, such as race horses or racing dogs. An animal (or person) infected with an adipogenic adenovirus may not be able to achieve as good a performance as an uninfected, so testing for adipogenic adenoviruses may be used as a predictor of performance quality.

Finally, increased intramuscular lipid in heart muscle may alter cardiac function, produce cardiomyopathy and congestive heart failure. Studies have showed that accumulation of excess fatty acids and triglycerides within heart muscle is associated with cardiac insulin resistance and cardiac dysfunction.

A further embodiment of the invention is related to using adipogenic adenoviruses status to predict pulmonary dysfunction. Also, a vaccine against adenoviruses will prevent pulmonary dysfunction.

It has been known for many years that obesity is associated with pulmonary disease such as asthma and emphysema. The mechanisms of this association are not clear. It is known that the lungs make FAS and synthesize lipids. Therefore, the finding that adipogenic adenoviruses can cause lung disease may be associated with the production of FAS in the lungs by adenoviruses. Studies have indicated that Ad-5 infection doubles the number of macrophages in the lung of guinea pigs. The combination of smoking and Ad-5 quadruples the number of macrophages. Latent viral infections were present in patients with asthma and emphysema and Ad-5 E1A protein in the lungs was correlated with inflammation in asthma and emphysema patients.

An embodiment of the invention is using adipogenic adenovirus status to predict brain and nervous system dysfunction. Also, a vaccine against adenoviruses may be used to prevent brain and nervous system dysfunction.

Adipogenic viruses infect brain tissue. It is well known that the nerves and brain make FAS. Obesity is linked to adverse neurocognitive outcome, including reduced cognitive functioning and Alzheimer's disease. Studies have demonstrated that BMI was inversely related to performance on all cognitive tests and there was no evidence of a BMI×age interaction. There is an increased prevalence of Alzheimer's disease in obesity. Abeta42, a type of amyloid that is deposited in Alzheimer's patients, correlated with BMI. Obese people may have about a 74% higher chance of dementia. Other studies have demonstrated that an Ad-5 vector that has been used in gene therapy caused inflammation of the brain. Wild type Ad-5 has been reported to cause obesity and we have noted that an Ad-5 vector that is used for gene transfer retains its ability to stimulate SREBP-1 and FAS synthesis in hepatocytes.

Accordingly, these data support the concept that adipogenic adenoviruses may increase lipogenic enzymes in the brain and nerves, produce excess fatty acid and triglycerides, and result in dysfunction.

An aspect of the invention is that testing for adipogenic adenoviruses may be used to predict adrenal dysfunction. Also, a vaccine against adenoviruses may be used to prevent adrenal dysfunction.

Obesity is known to significantly affect adrenal gland function. There is an increased secretion of aldosterone, but without renin, which may be associated with hypertension. Studies have demonstrated that adrenal function was not normal in obese women, but differed with abdominal fat distribution. Adrenal hormones use cholesterol as a substrate for production, and with the changes of adipogenic adenoviruses in both intracellular fatty acids and cholesterol metabolism, the use of a test to detect adipogenic adenoviruses may be a predictor of adrenal dysfunction.

Exemplary screening immunoanalytical techniques include without limitation, standard virus neutralization assay techniques or enzyme immunoassay techniques well known in the art. Techniques for raising and purifying antibodies against these viruses or fragments thereof (e.g., fiber protein or fragments thereof), or proteins (or fragments thereof) from these viruses for use in these immunoassay techniques may be prepared by conventional techniques are well known in the art. In a specific embodiment of the invention, antibodies will immunoprecipitate adenovirus virus or adenovirus proteins from solution as well as react with these proteins on Western or immunoblots or polyacrylamide gels. In another specific embodiment, antibodies will detect the presence of adenovirus or adenovirus proteins in frozen tissue sections, using immunocytochemical techniques. Specific embodiments relating to methods for detecting adenovirus or adenovirus proteins include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies.

Similarly, the nucleic acid probe hybridization assay techniques used in these methods of the invention will be standard techniques (optionally after amplification of DNA or RNA extracted from a sample of blood, other body fluid, feces, tissue or organ) using nucleic acid probes (and primers if amplification is employed) made available by the obesity-causing viruses identified and made available by the present invention. The sequences of nucleic acids characteristic of these viruses can be determined by standard techniques once the viruses are conventionally isolated, and probes and primers that are specific for the viruses and that provide the basis for nucleic acid probes and primers that can be used in nucleic acid based assays for the viruses are prepared using conventional techniques on the basis of the sequences.

For example, in order to detect the presence of an adenovirus predisposing an individual to obesity, a biological sample such as blood is prepared and analyzed for the presence or absence of adenovirus proteins, such as the Ad-36 fiber coat protein sequences. Results of these tests and interpretive information are returned to the health care provider for communication to the tested individual. Such diagnoses may be performed by diagnostic laboratories, or alternatively, diagnostic kits are manufactured and sold to health care providers or to private individuals for self-diagnosis.

Initially, screening involves amplification of the relevant adenovirus sequences. In a specific embodiment of the invention, the screening method involves a non-PCR based strategy. Such screening methods include two-step label amplification methodologies that are well known in the art. Both PCR and non-PCR based screening strategies can detect target sequences with a high level of sensitivity.

One embodiment of the invention relates to target amplification. Here, the target nucleic acid sequence is amplified with polymerase. One specific method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired to extract the nucleic acids. The sample nucleic acid may be prepared in various ways to facilitate detection of the target sequence, e.g., denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques well known in the art.

Analyte nucleic acid and probe are incubated under conditions which promote stable hybrid formation of the target sequence in the analyte. The region of the probes which is used to bind to the analyte can be made completely complementary to the targeted region of the adenovirus of interest, and in particular the fiber coat protein. Therefore, high stringency conditions are desirable in order to prevent false positives. However, conditions of hig stringency are used only if the probes are complementary to regions of the adenovirus. The stringency of hybridization is determined by a number of factors during hybridization and during the washing procedure, including temperature, ionic strength, base composition, probe length, and concentration of formamide.

Detection, if any, of the resulting hybrid is usually accomplished by the use of labeled probes. Alternatively, however, the probe may be unlabeled, but may be detectable by specific binding with a ligand which is labeled, either directly or indirectly. Suitable labels, and method for labeling probes and ligands are well known in the art, and include, for example, radioactive labels which may be incorporated by known methods (e.g., nick translation, random priming or kinasing), biotin, fluorescent groups, chemiluminescent groups (e.g., dioxetanes) enzymes, antibodies, gold nanoparticles and the like. Variations of this basic scheme are known in the art, and include those variations that facilitate separation of the hybrids to be detected from extraneous materials and/or that amplify the signal from the labeled moiety.

As noted above, non-PCR based screening assays are also contemplated by this invention. This procedure hybridizes a nucleic acid probe (or analog such as a methyl phosphonate backbone replacing the normal phosphodiester) to the low level DNA target. This probe may have an enzyme covalently linked to the probe, such that the covalent linkage does not interfere with the specificity of the hybridization. The enzyme-probe-conjugate-target nucleic acid complex can then be isolated away from the free probe conjugate and a substrate is added for enzyme detection. Enzymatic activity is observed as a change in color development or luminescent output resulting in about a $10^3$ to about a $10^6$ increase in sensitivity.

Two-step label amplification methodologies are known in the art. These assays work on the principle that a small ligand (such as digioxigenin, biotin, or the like) is attached to a nucleic acid probe capable of specific binding the adenovirus sequence region of interest. In one example, the small ligand attached to the nucleic acid probe is specifically recognized by an antibody-enzyme conjugate. In one embodiment of this example, digioexigenin is attached to the nucleic acid probe. Hybridization is detected by an antibody-alkaline phosphatase conjugate which turns over a chemiluminescent substrate. In a second example, the small ligand is recognized by a second ligand-enzyme conjugate that is capable of specifically complexing to the first ligand. A well known embodiment of this example is the biotin-avidin type interactions.

It is also contemplated within the scope of this invention that the nucleic acid probe assays of this invention will employ a cocktail of nucleic acid probes capable of detecting various species of adenoviruses. Thus, in one example to detect the presence of ad-36, ad-37 and/or ad-5, for example, in a biological sample, more than one probe complementary of the targeted regions of interest in the various types of adenovirus may be employed.

As the skilled will understand, more than one strain of obesity-causing virus may be tested for simultaneously in an immunological or nucleic acid-based assay method for testing for virus in accordance with the invention and kits may be assembled to facilitate carrying out the methods for a particular virus or a plurality of them.

The invention has been disclosed broadly and illustrated in reference to representative embodiments described above. Those skilled in the art will recognize that various modifications can be made to the present invention without departing from the spirit and scope thereof. Without further elaboration, it is believed that one skilled in the art, using the preceding description, can utilize the present invention to the fullest extent. The following examples are illustrative only, and not limiting of the remainder of the disclosure in any way whatsoever.

EXAMPLES

Specific Example 1

Blood samples from 502 humans in separate populations from three cities: Madison, Wis., Naples, Fla., and New York City, N.Y., were measured for Ad-36 infection. The definition of obesity was a BMI greater than about 30 kg/m$^2$ and the population was divided into obese and non-obese subjects. The prevalence of Ad-36 antibodies in serum obese subjects was about 30% and in non-obese was about 11% (i.e., a 3:1 ratio) (FIG. 13).

Figure 14:
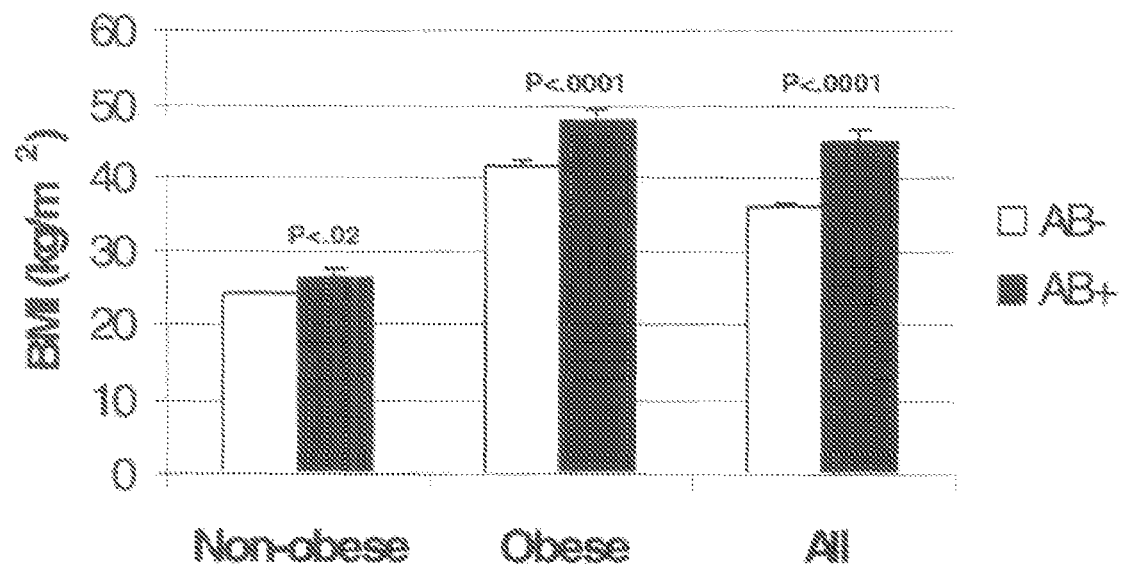
FIG. 14 is a chart showing body mass index in 502 individuals from three U.S. cities according to status of infection with Ad-36. Overall, BMI was about 9 units higher in infected versus uninfected people (p<0.0001). Infected individuals of both obese and non-obese groups were significantly heavier than the uninfected in each group.

When the subjects were divided into antibody positive versus antibody negative, the antibody positive were observed to be about 9 BMI units heavier (i.e., greater than about 50 pounds)($p<0.001$) (FIG. 14).

Moreover, serum cholesterol and triglycerides were lower in antibody positive humans (less than about −35 mg/dl, $p<0.001$), exactly the same reductions observed in prospectively infected monkeys. There were no correlations of antibodies to Ad-2 or Ad-31 with either body composition or serum cholesterol and triglycerides in humans, implying that the effects of Ad-36 are specific and are not common to all human adenoviruses.

A second study was performed in 28 twin pairs discordant for Ad-36 antibodies. Normally twins track body weight and BMI closely, but the Ad-36 antibody positive twins were fatter than their Ad-36 antibody negative co-twin ($p<0.04$) (FIG. 15).

In conclusion, these findings show that Ad-36 causes obesity in animals and humans.

Specific Example 2

Very strong evidence of an association of Ad-36 with cancer comes from studies at the University of Wisconsin. Banked serum from 128 subjects with breast cancer and 37 subjects with prostate cancer was obtained, and assayed for Ad-36 antibodies using a serum neutralization assay. It was observed that 51% of the patients with prostate cancer and 50% of the breast cancer patients were positive for Ad-36 antibodies. However, since the samples were anonymous, no data on obesity, type or stage of cancer, or presence of metastases. From data on Ad-36 antibodies in obese and non-obese individuals it was estimated that about 14% of the general population had Ad-36 antibodies. Thus, there is an almost four fold increase in the prevalence of Ad-36 antibodies in both breast and prostate cancer patients.

Specific Example 3

Figure 16:
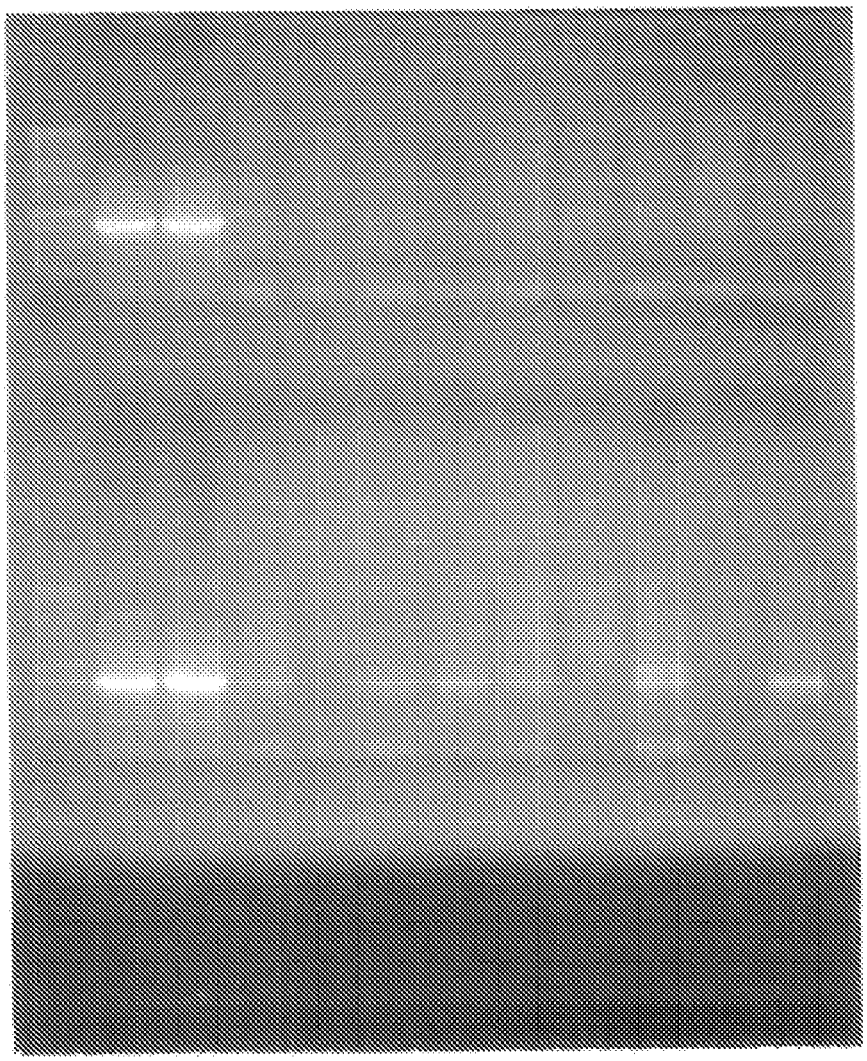
FIG. 16 is a gel showing the presence of Ad-36 DNA in prostate cancer tissue.
Figure 17:
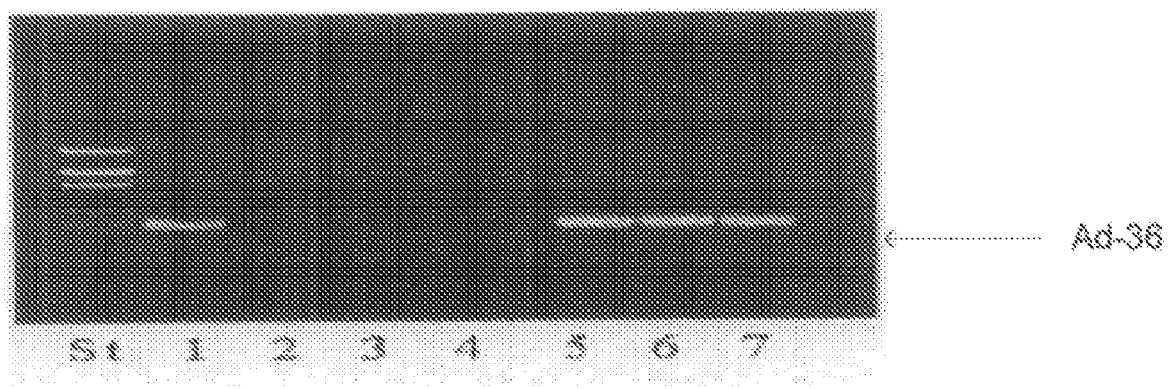
FIG. 17 is a gel showing the presence of Ad-36 DNA in monkeys.

Prostate cancer tissue from 18 patients was obtained and assayed for Ad-36 DNA by nested polymerase chain reaction assay (PCR) using primers made to unique DNA sequences in the Ad-36 fiber protein genome. Eleven of the 18, or 61%, had Ad-36 DNA in the cancer tissue. FIG. 16 shows a PCR gel demonstrating the presence of Ad-36 DNA in prostate cancer tissues. As noted above, Ad-36 DNA in multiple tissues of experimental animals was found, particularly in adipose tissue using nested PCR with primers made from unique DNA sequences in the Ad-36 fiber protein genome. FIG. 17 shows a PCR gel from DNA extracted from adipose tissue of monkeys infected with Ad-36. All three of the infected monkeys, but none of the controls, have viral DNA present.

Specific Example 4

This example shows the use of Ad-36 lab test as a marker to identify individuals at risk of developing cancer: People with cancer have a much higher prevalence of a positive Ad-36 lab test than do non-cancer patients. We tested 128 women with breast cancer and 37 men with prostate cancer and compared the results to 502 non-cancer patients. Of the total of 165 cancer patients, 83 (50%) had a positive Ad-36 test (50% of the breast cancer patients and 51% of the prostate cancer patients). Based on the prevalence of obesity in the US population, the data of the 502 non-cancer subjects showed that 17% of the non-cancer subjects had a positive Ad-36 test. If only those non-cancer subjects from Wisconsin are considered (since all the cancer patients were from Wisconsin, this is a better comparison), 14% of the non-cancer subjects had a positive Ad-36 test. Thus, almost 4 times as many cancer patients were positive compared to the non-cancer patients.

Specific Example 5

Adipose tissue from 9 humans at autopsy at the University of Wisconsin Hospital was obtained and assayed for Ad-36 DNA. Seven of the 9 had Ad-36 DNA in the adipose tissue. These data demonstrate that Ad-36 DNA may isolated from human and animal adipose tissue and more importantly, that the presence of Ad-36 DNA in tissues is a marker for post Ad-36 infection. Since the Ad-36 DNA appeared in multiple tissues of infected animals, it seems clear that the initial viremia results in infection of most of the tissues of the body.

Therefore, as described in the methods Section as described in Specific Example 6, below, cancer tissues or adipose tissue from cancer may be obtained from patients to test for the presence of Ad-36 DNA.

Specific Example 6

Samples are assayed for Ad-36 DNA in samples of breast and prostate tissue from cancer patients and non-cancer patients to determine if the prevalence of infection with Ad-36 is greater in cancer patients. Ad-36 status may be correlated with the presence of cancer and may be correlated with stage of cancer, presence of metastases, and prognosis of cancer victims. A vaccine against Ad-36 may prevent Ad-36 induced cancers.

Experimental Design

Anonymous samples of tissue and complete medical information are obtained from the NCI resource banks, the NCI Cooperative Human Tissue Network (CHTN) and the NCI Cooperative Breast Cancer Tissue Resource (CBCTR). The samples are assayed for Ad-36 DNA by nested PCR assay as described below. Alternatively, if DNA samples not are available, they are may ordered. If DNA has not been extracted from the samples, it may be as described below.

To evaluate breast cancer, samples of breast cancer tissue or adipose tissue near the breast from 100 women with cancer are compared with breast tissue or adipose tissue from 50 women undergoing breast surgery who do not have cancer. As noted above, if breast cancer tissue is not available, adipose tissue from near the breast is acceptable. Actual breast tissue is not critical as Ad-36 DNA appears in all tissues after infection, so adipose tissue is suitable.

To evaluate prostate cancer, samples of prostate cancer from 100 men is compared to prostate tissue from men undergoing surgery for benign prostatic hypertrophy (BPH).

Both NCI tissue banks have information on age, menopausal status of female patients, height, weight, family history of breast or prostate cancer, type and stage of cancer, presence of metastases, and in some cases, survival time. Because breast cancer associated with obesity is more prevalent in postmenopausal women, non-cancer subjects are matched as well as possible for age. It may be expected that prostate cancer patients from whom we obtain samples will be in the older age group (>50 years) because this is the population in which prostate cancer and BPH occurs. It may be very unlikely that we will have any tissues from pediatric patients as breast and prostate cancers are so rare in them.

Laboratory techniques: The procedures that will be needed for this protocol are published in the medical literature are understood by one of relevant skill in the art. A brief summary of each is given below:

Culture of Ad-36: Viral preparations are grown in tissue culture as previously described using A549 human bronchial carcinoma cells. A549 cells are obtained from American Type Culture Collection (ATCC, Rockville, Md.). Minimum Essential Media Eagle (MEM) (Cat #M-0643, Sigma Chemicals) with non-essential amino acids, Earle's salts and L-glutamine are used for growing A549 cells. Work stocks are grown in A549 cells using MEM with 10% fetal bovine serum (FBS) and 2.9% $NaHCO_3$ (v/v) at pH 7.4.

Plaque forming units assay: Titers of Ad-36 virus are determined using A549 cells by this assay. Starting with 100 μl of virus suspension and 900 ul of media, serial 10 fold dilutions are made. A549 cells are grown to confluence in 6 well plates and 3 wells are used for each dilution. Three wells are used as the blank control and are not infected with the virus suspension. Media is removed from each cell and 100 ul of the serially diluted virus suspension are pipetted out in the wells. The plates are incubated at 37° C., shaking gently every 15 min. After 1 h of incubation, the viral suspension from the wells is removed and discarded. The wells are overlaid with about 3 ml of 1% agar in media per well, with 1× antibiotic-antimycotic solution. The plates are inverted and incubated at 37° C. for 8 days until plaques appear. After 8 days, wells are stained overnight with about 1 ml of crystal violet per well. The next day, the number of plaques formed is counted after removing the agar. The number of plaques formed×dilution of viral suspension used gives PFU/100 uL of inoculum used. This is multiplied by 10 to express PFU/mL.

Tissue culture infectivity dose (TCID50)(66-72): The titer of the work stocks that cause a cytopathic effect (CPE) in 50% of the wells containing A549 cells are calculated and expressed as tissue culture infectivity dose (TCID-50) units per ml. TCID-50 of the work stocks are determined using serial ten fold dilutions of the virus work stock. TCID50 is calculated by serially diluting the virus stock solution and inoculating cells with the dilutions to find out the reciprocal of the highest dilution of virus which causes cytopathic effect (CPE) in 50% of the cells inoculated. Titers are calculated after the cells inoculated with the virus dilutions are incubated at 37° C. for 8 days.

Nested PCR assay: The nested PCR detects Ad-36 DNA in biological samples. As previously described, four primers were designed to unique regions of the Ad-36 fiber protein gene for use in a nested PCR assay for detection of viral DNA. Sequences of primers:

```
outer forward primer
    (5'-GTCTGGAAAACTGAGTGTGGATA),       (SEQ ID No:1)

outer reverse primer
    (5=-ATCCAAAATCAAATGTAATAGAGT),     (SEQ ID No:2)

inner forward primer
    (5=-TTAACTGGAAAAGGAATAGGTA),       (SEQ ID No.3)

inner reverse primer
    (5=-GGTGTTGTTGGTTGGCTTAGGATA).     (SEQ ID No.4)
```

DNA is isolated from human breast and prostate tissues using a QIAamp Tissue Kit (Qiagen, Valencia, Calif., USA; Cat #29304). Negative PCR controls are water and DNA from A549 cells. Positive PCR control is DNA from Ad-36 infected A-549 cells. DNA is denatured for 2 min at 95° C. and subjected to 35 cycles of PCR (94° C. for 1 min, 55° C. for 1 min, 72° C. for 2 min) followed by incubation at 72° C. for 5 min. PCR products are visualized on a 1% agarose gel with a size marker.

This assay was developed at the University of Wisconsin and at that time the conditions were optimized for temperature, magnesium concentration, and number of cycles in samples consisting of animal and human tissues, and of 3T3-L1 cells. Samples of the PCR products are extracted from the gels and are sent to the University of Wisconsin Biotech Center for sequencing to insure that the amplified DNA sequences were from the targeted regions. The Biotech Center confirmed their accuracy. These quality control procedures are repeated to conform to CLIA specifications and good laboratory practice. DNA sequencing of two positive samples each of breast cancer and of prostate cancer and the A549 positive control DNA samples are performed to insure accuracy of the amplifications.

Statistical analyses and Power calculations: Statistical assistance is available from the Department of Statistical Sciences and Operations Research of the Virginia Commonwealth University.

Power calculations: Power analysis was performed using preliminary data on the prevalence of Ad-36 antibodies in the general population versus in cancer patients in Madison, Wis. It was shown that 50% and 51% of breast cancer and prostate cancer patients, respectively, at the University of Wisconsin Hospital had antibodies to Ad-36. In a sample of volunteers from the general population and the Obesity Treatment Program at the University of Wisconsin, 247 subjects were evaluated, of whom 183 were obese and 64 were non-obese. The prevalence of Ad-36 antibodies was 20% and 11%, respectively. CDC figures show that approximately 31% of adult Americans are obese and 69% are non-obese. Using these numbers, it was estimated that the prevalence of Ad-36 antibodies in the general population of Madison, Wis., was 13.8%. Thus, the prevalence of Ad-36 in cancer patients is almost fourfold higher. Using these figures, the power calculations revealed that 32 subjects per group is necessary to achieve a power of 80% at the 0.05 level to determine a difference in prevalence of Ad-36 in cancer vs non-cancer patients. About 50% of both breast and prostate cancer patients may be expected to be Ad-36 antibody positive based on the preliminary data. However, it may be possible that the Ad-36 prevalence may be lower in the banked samples from the NCI tissue banks (or Asterand tissue bank), and this would affect the power significantly. Therefore, 100 cancer subjects and 50 non-cancer subjects may be certain to have sufficient power.

Statistical analyses: Chi-square analysis will be used to determine if the prevalence of Ad-36 DNA in cancer subjects is greater than in non-cancer subjects. The number of subjects is relatively small for multiple regression analyses and we do not expect to see significant correlations unless the effect is powerful.

Specific Example 7

The cDNA sequence of the Ad-36 genome was screened against all known cDNA sequences and two 25-base sequences and one 28-base sequence were found, all lying in the fiber-encoding sequence that were unique to Ad-36. These three sequences are as follows:

```
SEQ ID NO: 5:  5'-AGTTGAAACAGCAAGAGACTCAAAG
SEQ ID NO: 6   5'-GGTACTGGATCAAGTGCACATGGAG
SEQ ID NO: 7   5'-TTGAAACAGCAAGAGACTCAAAGCTAAC
```

Sequence 3 above was employed a probe for Ad-36 in a conventional nuclei acid probe hybridization assay of DNA isolated from four chickens, two of which had been infected with the virus and became obese and two of which had not been infected and were not obese. DNA hybridizing to the probe was observed with only the DNA from the two infected chickens. The assay involved direct detection and was by capillary electrophoresis using laser-induced fluorescence for detection. More particularly, a replaceable polyacrylamide matrix was employed in the electrophoretic separation and detection employed a dual system with 5'-labeling of the oligo and thiazole orange intercalator in the buffer system.

The skilled will understand that probes, and primers when amplification is also used, of between about 15 and 30 bases in length are advantageously employed to provide suitable specificity and sensitivity. Amplification methods using PCR and variations thereof maybe employed, as well known in the art.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in molecular biology or related fields are intended to be within the scope of the appended claims.

The disclosures of all references and publications cited above are expressly incorporated by reference in their entireties to the same extent as if each were incorporated by reference individually.

What is claimed is:

1. A method for predicting cancer aggressiveness in a subject having an abnormality compatible with a tumor, said method comprising the steps of:
   obtaining a sample from the subject;
   assaying the sample to determine whether the subject is infected with an adipogenic adenovirus; and
   predicting a more aggressive form of cancer in a subject infected with an adipogenic relative to a subject not infected with an adipogenic adenovirus.

2. The method of claim 1, wherein said step of assaying the sample comprises the steps of:
   screening for the presence of antibodies specific to the adipogenic adenovirus in the sample; and
   determining the presence of antibodies specific to the adipogenic adenovirus in the sample.

3. The method of claim 1, wherein the adipogenic adenovirus is one or more adipogenic viruses selected from the group consisting of adenovirus type 5, adenovirus type 36, and adenovirus type 37.

4. The method of claim 1, wherein the cancer is selected from the group consisting of breast, prostate, uterus, ovary, colon, kidney, pancreas, and lung.

5. The method of claim 1, wherein the subject is a human.

6. The method of claim 1, wherein the subject is an animal.

7. The method of claim 2, wherein the antibodies in said determining step are specific to one or more peptide encoded by the nucleic acid sequences selected from the group consisting of SEQ ID NO.:5, SEQ ID NO.:6, and SEQ ID NO.:7.

8. The method of claim 2, wherein said screening step is performed by using a method selected from the group consisting of serum neutralization assay and ELISA.

9. The method of claim 1, wherein the sample is selected from the group consisting of a biological sample, body fluid, a tissue sample, an organ sample, feces, blood, saliva, and any combination thereof.

10. The method of claim 1, wherein the more aggressive form of cancer in the subject infected with the adipogenic adenovirus relative to the subject not infected with the adipogenic adenovirus is selected from the group consisting of higher tumor grade, larger tumor volume, advancing clinical stage, increased Gleason's score, and higher grade dysplasia.

* * * * *

SEQUENCE LISTING

```
<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtctggaaaa ctgagtgtgg ata                                              23

<210> SEQ ID NO 2
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
atccaaaatc aaatgtaata gagt                                              24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttaactggaa aaggaatagg ta                                                22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtgttgttg gttggcttag gata                                              24

<210> SEQ ID NO 5
<211> LENGTH: 25
<212> TYPE: DNA
<213> ORGANISM: Adenovirus type 36

<400> SEQUENCE: 5
agttgaaaca gcaagagact caaag                                             25

<210> SEQ ID NO 6
<211> LENGTH: 25
<212> TYPE: DNA
<213> ORGANISM: Adenovirus type 36

<400> SEQUENCE: 6
ggtactggat caagtgcaca tggag                                             25

<210> SEQ ID NO 7
<211> LENGTH: 28
<212> TYPE: DNA
<213> ORGANISM: Adenovirus type 36

<400> SEQUENCE: 7
ttgaaacagc aagagactca aagctaac                                          28
```